United States Patent
Burtrum et al.

(10) Patent No.: US 10,711,066 B2
(45) Date of Patent: Jul. 14, 2020

(54) ANTI-CANINE PLATELET DERIVED GROWTH FACTOR RECEPTOR ALPHA ANTIBODY

(71) Applicant: Elanco US Inc., Indianapolis, IN (US)

(72) Inventors: Douglas Bryan Burtrum, New York, NY (US); Dale Lincoln Ludwig, Rockaway, NJ (US); Juqun Shen, Flushing, NY (US); Cheng Wang, Forest Hills, NY (US)

(73) Assignee: Elanco US Inc., Greenfield, IN (US)

( * ) Notice: Subject to any disclaimer, the term of this patent is extended or adjusted under 35 U.S.C. 154(b) by 69 days.

(21) Appl. No.: 16/318,944

(22) PCT Filed: Jul. 20, 2017

(86) PCT No.: PCT/US2017/042996
§ 371 (c)(1),
(2) Date: Jan. 18, 2019

(87) PCT Pub. No.: WO2018/022407
PCT Pub. Date: Feb. 1, 2018

(65) Prior Publication Data
US 2019/0300612 A1      Oct. 3, 2019

Related U.S. Application Data

(60) Provisional application No. 62/367,808, filed on Jul. 28, 2016.

(51) Int. Cl.
*C07K 16/22* (2006.01)
*C07K 16/28* (2006.01)

(52) U.S. Cl.
CPC ...... *C07K 16/2863* (2013.01); *C07K 2317/24* (2013.01); *C07K 2317/33* (2013.01); *C07K 2317/40* (2013.01); *C07K 2317/41* (2013.01); *C07K 2317/53* (2013.01); *C07K 2317/565* (2013.01); *C07K 2317/76* (2013.01); *C07K 2317/92* (2013.01)

(58) Field of Classification Search
None
See application file for complete search history.

(56) References Cited

FOREIGN PATENT DOCUMENTS

| WO | 2006138729 | 12/2006 |
|---|---|---|
| WO | 2016003789 | 1/2016 |

OTHER PUBLICATIONS

Arico et al. J. Comp. Path. 151: 322-328, 2014.*
Patent Cooperation Treaty International Search Report and the Written Opinion of the International Searching Authority pertaining to International Application No. PCT/2017/042996; dated Sep. 29, 2017.
Maniscalco, Lorella, et al. "PDGFs and PDGFRs in canine osteosarcoma: new targets for innovative therapeutic strategies in comparative oncology." The Veterinary Journal 195, No. 1 (2013): 41-47.
Kabat et al., Sequences 20 of Proteins of Immunological Interest, Fifth Edition, U.S. Department of Health and Human Services, NIH Publication No. 91-3242 (1991).
Chothia, Cyrus, and Arthur M. Lesk. "Canonical structures for the hypervariable regions of immunoglobulins." Journal of molecular biology 196, No. 4 (1987): 901-917.
North et al., A New Clustering of Antibody CDR Loop Conformations, Journal of Molecular Biology, 406:228-256 (2011).

* cited by examiner

*Primary Examiner* — Christine J Saoud
(74) *Attorney, Agent, or Firm* — David L. Pflugh

(57) ABSTRACT

The present disclosure relates to anti-canine platelet derived growth factor receptor alpha antibodies binding to canine platelet derived growth factor receptor alpha.

6 Claims, No Drawings
Specification includes a Sequence Listing.

derived

SEQUENCE LISTING

```
<160> NUMBER OF SEQ ID NOS: 39

<210> SEQ ID NO 1
<211> LENGTH: 439
<212> TYPE: PRT
<213> ORGANISM: Artificial Sequence
<220> FEATURE:
<223> OTHER INFORMATION: Synthetic Construct

<400> SEQUENCE: 1

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gln Ser Ser
            20                  25                  30

Ser Tyr Tyr Trp Gly Trp Leu Arg Gln Ser Pro Gly Lys Gly Leu Glu
        35                  40                  45

Trp Ile Gly Ser Phe Phe Tyr Thr Gly Ser Thr Tyr Tyr Asn Pro Ser
```

```
            50                  55                  60
Leu Arg Ser Arg Leu Thr Ile Ser Val Asp Thr Ser Lys Asn Gln Phe
 65                  70                  75                  80

Ser Leu Met Leu Ser Ser Val Thr Ala Ala Asp Thr Ala Val Tyr Tyr
                     85                  90                  95

Cys Ala Arg Gln Ser Thr Tyr Tyr Asp Gly Ser Gly Asn Tyr Tyr Gly
                100                 105                 110

Trp Phe Asp Arg Trp Asp Gln Gly Thr Leu Val Thr Val Ser Ser Ala
                115                 120                 125

Ser Thr Thr Ala Pro Ser Val Phe Pro Leu Ala Pro Ser Cys Gly Ser
            130                 135                 140

Thr Ser Gly Ser Thr Val Ala Leu Ala Cys Leu Val Ser Gly Tyr Phe
145                 150                 155                 160

Pro Glu Pro Val Thr Val Ser Trp Asn Ser Gly Ser Leu Thr Ser Gly
                    165                 170                 175

Val His Thr Phe Pro Ser Val Leu Gln Ser Ser Gly Leu Tyr Ser Leu
                180                 185                 190

Ser Ser Met Val Thr Val Pro Ser Ser Arg Trp Pro Ser Glu Thr Phe
            195                 200                 205

Thr Cys Asn Val Ala His Pro Ala Ser Lys Thr Lys Val Asp Lys Pro
210                 215                 220

Val Pro Lys Arg Glu Ser Gly Arg Val Pro Arg Pro Asp Cys Pro
225                 230                 235                 240

Lys Cys Pro Ala Pro Glu Met Leu Gly Gly Pro Ser Val Phe Ile Phe
                245                 250                 255

Pro Pro Lys Pro Lys Asp Thr Leu Leu Ile Ala Arg Thr Pro Glu Val
                260                 265                 270

Thr Cys Val Val Val Asp Leu Asp Pro Glu Asp Pro Glu Val Gln Ile
                275                 280                 285

Ser Trp Phe Val Asp Gly Lys Gln Met Gln Thr Ala Lys Thr Gln Pro
            290                 295                 300

Arg Glu Glu Gln Phe Asn Gly Thr Tyr Arg Val Val Ser Val Leu Pro
305                 310                 315                 320

Ile Gly His Gln Asp Trp Leu Lys Gly Lys Gln Phe Thr Cys Lys Val
                325                 330                 335

Asn Asn Lys Ala Leu Pro Ser Pro Ile Glu Arg Thr Ile Ser Lys Ala
                340                 345                 350

Arg Gly Gln Ala His Gln Pro Ser Val Tyr Val Leu Pro Pro Ser Arg
            355                 360                 365

Glu Glu Leu Ser Lys Asn Thr Val Ser Leu Thr Cys Leu Ile Lys Asp
            370                 375                 380

Phe Phe Pro Pro Asp Ile Asp Val Glu Trp Gln Ser Asn Gly Gln Gln
385                 390                 395                 400

Glu Pro Glu Ser Lys Tyr Arg Thr Thr Pro Pro Gln Leu Asp Glu Asp
                405                 410                 415

Gly Ser Tyr Phe Leu Tyr Ser Lys Leu Ser Val Asp Lys Ser Arg Trp
                420                 425                 430

Gln Arg Gly Asp Thr Phe Ile
            435

<210> SEQ ID NO 2
<211> LENGTH: 1467
<212> TYPE: DNA
<213> ORGANISM: Artificial Sequence
```

<220> FEATURE:
<223> OTHER INFORMATION: Synthetic Construct

<400> SEQUENCE: 2

```
aagcttgccg ccaccatggg ctggtcttgc atcattctgt tcctggtcgc aacagccact    60
ggagtgcact cccagctgca gctgcaggag agcggacctg gactggtcaa gccatctgaa   120
accctgagtc tgacctgtac agtgagcggc ggatctatcc agtccagctc ttactattgg   180
ggctggctgc ggcagtctcc agggaaaggt ctggagtgga ttgggagctt cttttacaca   240
ggttctactt actataaccc cagtctgagg tcacggctga ccatctcagt ggacacatcc   300
aagaatcagt tttccctgat gctgagttca gtcacagccg ctgatactgc cgtgtactat   360
tgcgctcgac agagtaccta ctatgacggc tcaggaaact attacgggtg gttcgaccgt   420
tgggatcagg gtaccctggt cacagtgtcc agcgcaagca ccacagcacc atccgtgttc   480
cccctggccc ctagctgcgg gagtacctca ggttccacag tcgctctggc atgtctggtg   540
agtgggtatt tccctgagcc agtcaccgtg tcatggaata gcggctctct gacttctgga   600
gtccacacct ttcctagtgt gctgcagtct agtggcctgt actctctgtc atccatggtc   660
actgtgccca gctccaggtg gccttctgaa actttcacct gcaacgtggc ccatccagct   720
agtaagacaa agtggacaa gcccgtgcct aaacgcgaga gtggaagagt gccacgcccc   780
cctgattgcc ccaagtgtcc agctcccgaa atgctggggg gtccttccgt gttcatcttt   840
ccacccaagc caaaagacac cctgctgatt gcaagaactc ctgaggtgac ctgcgtggtc   900
gtggacctgg accccgagga ccccgaagtc cagatttcct ggttcgtgga tgggaagcag   960
atgcagactg ccaaaaccca gcccagagag gaacagttta cggtacata tcgcgtcgtg  1020
agcgtgctgc ctatcggcca ccaggactgg ctgaagggaa aacagtttac atgcaaggtg  1080
aacaataaag ctctgcccttc accaatcgag aggactattt ccaaggctcg ggacaggca  1140
catcagccca gcgtctatgt gctgcctcca agtcgagagg aactgtcaaa gaacacagtg  1200
tccctgactt gtctgatcaa agatttctttt ccccctgaca ttgatgtgga gtggcagagc  1260
aatggccagc aggagcctga atctaagtac cgcactaccc cacccccagct ggacgaagat  1320
ggcagctatt tcctgtactc caagctgagc gtggacaaat ctcgatggca gcgtggagat  1380
acctttatct gtgcagtgat gcacgaggcc ctgcacaatc attacacaca agaaagtctg  1440
tcacattccc ccggcaagtg agaattc                                      1467
```

<210> SEQ ID NO 3
<211> LENGTH: 462
<212> TYPE: PRT
<213> ORGANISM: Artificial Sequence
<220> FEATURE:
<223> OTHER INFORMATION: Synthetic Construct

<400> SEQUENCE: 3

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gln Ser Ser
            20                  25                  30

Ser Tyr Tyr Trp Gly Trp Leu Arg Gln Ser Pro Gly Lys Gly Leu Glu
        35                  40                  45

Trp Ile Gly Ser Phe Phe Tyr Thr Gly Ser Thr Tyr Tyr Asn Pro Ser
    50                  55                  60

Leu Arg Ser Arg Leu Thr Ile Ser Val Asp Thr Ser Lys Asn Gln Phe
65                  70                  75                  80
```

Ser Leu Met Leu Ser Ser Val Thr Ala Ala Asp Thr Ala Val Tyr Tyr
                85                  90                  95

Cys Ala Arg Gln Ser Thr Tyr Tyr Asp Gly Ser Gly Asn Tyr Tyr Gly
            100                 105                 110

Trp Phe Asp Arg Trp Asp Gln Gly Thr Leu Val Thr Val Ser Ser Ala
        115                 120                 125

Ser Thr Thr Ala Pro Ser Val Phe Pro Leu Ala Pro Ser Cys Gly Ser
    130                 135                 140

Thr Ser Gly Ser Thr Val Ala Leu Ala Cys Leu Val Ser Gly Tyr Phe
145                 150                 155                 160

Pro Glu Pro Val Thr Val Ser Trp Asn Ser Gly Ser Leu Thr Ser Gly
                165                 170                 175

Val His Thr Phe Pro Ser Val Leu Gln Ser Ser Gly Leu Tyr Ser Leu
            180                 185                 190

Ser Ser Met Val Thr Val Pro Ser Ser Arg Trp Pro Ser Glu Thr Phe
        195                 200                 205

Thr Cys Asn Val Ala His Pro Ala Ser Lys Thr Lys Val Asp Lys Pro
    210                 215                 220

Val Pro Lys Arg Glu Ser Gly Arg Val Pro Arg Pro Asp Cys Pro
225                 230                 235                 240

Lys Cys Pro Ala Pro Glu Met Leu Gly Gly Pro Ser Val Phe Ile Phe
                245                 250                 255

Pro Pro Lys Pro Lys Asp Thr Leu Leu Ile Ala Arg Thr Pro Glu Val
            260                 265                 270

Thr Cys Val Val Val Asp Leu Asp Pro Glu Asp Pro Glu Val Gln Ile
        275                 280                 285

Ser Trp Phe Val Asp Gly Lys Gln Met Gln Thr Ala Lys Thr Gln Pro
    290                 295                 300

Arg Glu Glu Gln Phe Asn Gly Thr Tyr Arg Val Val Ser Val Leu Pro
305                 310                 315                 320

Ile Gly His Gln Asp Trp Leu Lys Gly Lys Gln Phe Thr Cys Lys Val
                325                 330                 335

Asn Asn Lys Ala Leu Pro Ser Pro Ile Glu Arg Thr Ile Ser Lys Ala
            340                 345                 350

Arg Gly Gln Ala His Gln Pro Ser Val Tyr Val Leu Pro Pro Ser Arg
        355                 360                 365

Glu Glu Leu Ser Lys Asn Thr Val Ser Leu Thr Cys Leu Ile Lys Asp
    370                 375                 380

Phe Phe Pro Pro Asp Ile Asp Val Glu Trp Gln Ser Asn Gly Gln Gln
385                 390                 395                 400

Glu Pro Glu Ser Lys Tyr Arg Thr Thr Pro Pro Gln Leu Asp Glu Asp
                405                 410                 415

Gly Ser Tyr Phe Leu Tyr Ser Lys Leu Ser Val Asp Lys Ser Arg Trp
            420                 425                 430

Gln Arg Gly Asp Thr Phe Ile Cys Ala Val Met His Glu Ala Leu His
        435                 440                 445

Asn His Tyr Thr Gln Glu Ser Leu Ser His Ser Pro Gly Lys
    450                 455                 460

<210> SEQ ID NO 4
<211> LENGTH: 127
<212> TYPE: PRT
<213> ORGANISM: Artificial Sequence
<220> FEATURE:

<223> OTHER INFORMATION: Synthetic Construct

<400> SEQUENCE: 4

```
Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Gln Ser Ser
            20                  25                  30
Ser Tyr Tyr Trp Gly Trp Leu Arg Gln Ser Pro Gly Lys Gly Leu Glu
        35                  40                  45
Trp Ile Gly Ser Phe Phe Tyr Thr Gly Ser Thr Tyr Tyr Asn Pro Ser
    50                  55                  60
Leu Arg Ser Arg Leu Thr Ile Ser Val Asp Thr Ser Lys Asn Gln Phe
65                  70                  75                  80
Ser Leu Met Leu Ser Ser Val Thr Ala Ala Asp Thr Ala Val Tyr Tyr
                85                  90                  95
Cys Ala Arg Gln Ser Thr Tyr Tyr Asp Gly Ser Gly Asn Tyr Tyr Gly
            100                 105                 110
Trp Phe Asp Arg Trp Asp Gln Gly Thr Leu Val Thr Val Ser Ser
        115                 120                 125
```

<210> SEQ ID NO 5
<211> LENGTH: 381
<212> TYPE: DNA
<213> ORGANISM: Artificial Sequence
<220> FEATURE:
<223> OTHER INFORMATION: Synthetic Construct

<400> SEQUENCE: 5

```
cagctgcagc tgcaggagag cggacctgga ctggtcaagc catctgaaac cctgagtctg      60
acctgtacag tgagcggcgg atctatccag tccagctctt actattgggg ctggctgcgg     120
cagtctccag ggaaaggtct ggagtggatt gggagcttct tttacacagg ttctacttac     180
tataacccca gtctgaggtc acggctgacc atctcagtgg acacatccaa gaatcagttt     240
tccctgatgc tgagttcagt cacagccgct gatactgccg tgtactattg cgctcgacag     300
agtacctact atgacggctc aggaaactat tacgggtggt tcgaccgttg ggatcagggt     360
accctggtca cagtgtccag c                                               381
```

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

```
Thr Val Ser Gly Gly Ser Ile Gln Ser Ser Ser Tyr Tyr Trp Gly
1               5                   10                  15
```

<210> SEQ ID NO 7
<211> LENGTH: 45
<212> TYPE: DNA
<213> ORGANISM: Artificial Sequence
<220> FEATURE:
<223> OTHER INFORMATION: Synthetic Construct

<400> SEQUENCE: 7

```
acagtgagcg gcggatctat ccagtccagc tcttactatt ggggc                      45
```

<210> SEQ ID NO 8

<211> LENGTH: 16
<212> TYPE: PRT
<213> ORGANISM: Artificial Sequence
<220> FEATURE:
<223> OTHER INFORMATION: Synthetic Construct

<400> SEQUENCE: 8

Ser Phe Phe Tyr Thr Gly Ser Thr Tyr Tyr Asn Pro Ser Leu Arg Ser
1               5                   10                  15

<210> SEQ ID NO 9
<211> LENGTH: 48
<212> TYPE: DNA
<213> ORGANISM: Artificial Sequence
<220> FEATURE:
<223> OTHER INFORMATION: Synthetic Construct

<400> SEQUENCE: 9
agcttctttt acacaggttc tacttactat aaccccagtc tgaggtca                48

<210> SEQ ID NO 10
<211> LENGTH: 19
<212> TYPE: PRT
<213> ORGANISM: Artificial Sequence
<220> FEATURE:
<223> OTHER INFORMATION: Synthetic Construct

<400> SEQUENCE: 10

Ala Arg Gln Ser Thr Tyr Tyr Asp Gly Ser Gly Asn Tyr Tyr Gly Trp
1               5                   10                  15

Phe Asp Arg

<210> SEQ ID NO 11
<211> LENGTH: 57
<212> TYPE: DNA
<213> ORGANISM: Artificial Sequence
<220> FEATURE:
<223> OTHER INFORMATION: Synthetic Construct

<400> SEQUENCE: 11
gctcgacaga gtacctacta tgacggctca ggaaactatt acgggtggtt cgaccgt      57

<210> SEQ ID NO 12
<211> LENGTH: 217
<212> TYPE: PRT
<213> ORGANISM: Artificial Sequence
<220> FEATURE:
<223> OTHER INFORMATION: Synthetic Construct

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ala Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gln Gly Thr Lys Val Glu Ile Lys Arg Asn Asp Ala Gln

```
            100                 105                 110
Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215

<210> SEQ ID NO 13
<211> LENGTH: 732
<212> TYPE: DNA
<213> ORGANISM: Artificial Sequence
<220> FEATURE:
<223> OTHER INFORMATION: Synthetic Construct

<400> SEQUENCE: 13
aagcttgccg ccaccatggg ttggtcctgc atcattctgt tcctggtggc caccgctaca      60
ggcgtgcaca gcgaaatcgt cctgacccag tctcccgcca cactgagtct gtcacctggc     120
gagagagcca ccctgtcttg tcgcgcttcc caggccgtgt ccagctacct ggcatggtat     180
cagcagaagc tggacaggc cccaagactg ctgatctacg acgcttccaa ccgagcaaca     240
gggattccag ctcgtttctc tggcagtgga tcagggactg actttactct gaccatctct     300
agtctggagc ccgaagattt cgccgtgtac tattgccagc agcggagcaa ctggccccct     360
gcatttggtc agggcaccaa ggtggaaatt aaacgcaatg acgcacagcc tgccgtctac     420
ctgttccagc caagtcccga tcagctgcat acaggctccg ccagcgtggt ctgtctgctg     480
aacagctttt atccaaagga catcaatgtg aagtggaaag tggacggagt catccaggat     540
actgggattc aggagtccgt caccgaacag gacaaagatt ctacatatag tctgtcatcc     600
acactgacta tgagctctac cgagtacctg agtcacgaac tgtattcatg cgagatcact     660
cataagtcac tgccctccac cctgattaag tccttccaga ggtctgagtg tcagcgggtg     720
gattgagaat tc                                                         732

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ala Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
```

```
              50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Phe Gly Gln Gly Thr Lys Val Glu Ile Lys
            100                 105

<210> SEQ ID NO 15
<211> LENGTH: 321
<212> TYPE: DNA
<213> ORGANISM: Artificial Sequence
<220> FEATURE:
<223> OTHER INFORMATION: Synthetic Construct

<400> SEQUENCE: 15
gaaatcgtcc tgacccagtc tcccgccaca ctgagtctgt cacctggcga gagagccacc      60
ctgtcttgtc gcgcttccca ggccgtgtcc agctacctgg catggtatca gcagaagcct     120
ggacaggccc caagactgct gatctacgac gcttccaacc gagcaacagg gattccagct     180
cgtttctctg gcagtggatc agggactgac tttactctga ccatctctag tctggagccc     240
gaagatttcg ccgtgtacta ttgccagcag cggagcaact ggccccctgc atttggtcag     300
ggcaccaagg tggaaattaa a                                               321

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Arg Ala Ser Gln Ala Val Ser Ser Tyr Leu Ala
 1               5                  10

<210> SEQ ID NO 17
<211> LENGTH: 33
<212> TYPE: DNA
<213> ORGANISM: Artificial Sequence
<220> FEATURE:
<223> OTHER INFORMATION: Synthetic Construct

<400> SEQUENCE: 17
cgcgcttccc aggccgtgtc cagctacctg gca                                   33

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Tyr Asp Ala Ser Asn Arg Ala Thr
 1               5

<210> SEQ ID NO 19
<211> LENGTH: 24
<212> TYPE: DNA
<213> ORGANISM: Artificial Sequence
<220> FEATURE:
<223> OTHER INFORMATION: Synthetic Construct
```

<400> SEQUENCE: 19
tacgacgctt ccaaccgagc aaca                                          24

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gln Gln Arg Ser Asn Trp Pro Pro Ala
1               5

<210> SEQ ID NO 21
<211> LENGTH: 27
<212> TYPE: DNA
<213> ORGANISM: Artificial Sequence
<220> FEATURE:
<223> OTHER INFORMATION: Synthetic Construct

<400> SEQUENCE: 21
cagcagcgga gcaactggcc ccctgca                                       27

<210> SEQ ID NO 22
<211> LENGTH: 462
<212> TYPE: PRT
<213> ORGANISM: Artificial Sequence
<220> FEATURE:
<223> OTHER INFORMATION: Synthetic Construct

<400> SEQUENCE: 22

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Ser
            20                  25                  30

Ser Tyr Tyr Trp Gly Trp Leu Arg Gln Ser Pro Gly Lys Gly Leu Glu
        35                  40                  45

Trp Ile Gly Ser Phe Phe Tyr Thr Gly Ser Thr Tyr Tyr Asn Pro Ser
    50                  55                  60

Leu Arg Ser Arg Leu Thr Ile Ser Val Asp Thr Ser Lys Asn Gln Phe
65                  70                  75                  80

Ser Leu Met Leu Ser Ser Val Thr Ala Ala Asp Thr Ala Val Tyr Tyr
                85                  90                  95

Cys Ala Arg Gln Ser Thr Tyr Tyr Gly Ser Gly Asn Tyr Tyr Gly
            100                 105                 110

Trp Phe Asp Arg Trp Asp Gln Gly Thr Leu Val Thr Val Ser Ser Ala
        115                 120                 125

Ser Thr Thr Ala Pro Ser Val Phe Pro Leu Ala Pro Ser Cys Gly Ser
    130                 135                 140

Thr Ser Gly Ser Thr Val Ala Leu Ala Cys Leu Val Ser Gly Tyr Phe
145                 150                 155                 160

Pro Glu Pro Val Thr Val Ser Trp Asn Ser Gly Ser Leu Thr Ser Gly
                165                 170                 175

Val His Thr Phe Pro Ser Val Leu Gln Ser Ser Gly Leu Tyr Ser Leu
            180                 185                 190

Ser Ser Met Val Thr Val Pro Ser Ser Arg Trp Pro Ser Glu Thr Phe
        195                 200                 205

Thr Cys Asn Val Ala His Pro Ala Ser Lys Thr Lys Val Asp Lys Pro

```
                   210                 215                 220
Val Pro Lys Arg Glu Asn Gly Arg Val Pro Arg Pro Asp Cys Pro
225                 230                 235                 240

Lys Cys Pro Ala Pro Glu Met Leu Gly Gly Pro Ser Val Phe Ile Phe
                245                 250                 255

Pro Pro Lys Pro Lys Asp Thr Leu Leu Ile Ala Arg Thr Pro Glu Val
                260                 265                 270

Thr Cys Val Val Val Asp Leu Asp Pro Glu Asp Pro Glu Val Gln Ile
            275                 280                 285

Ser Trp Phe Val Asp Gly Lys Gln Met Gln Thr Ala Lys Thr Gln Pro
290                 295                 300

Arg Glu Glu Gln Phe Asn Gly Thr Tyr Arg Val Ser Val Leu Pro
305                 310                 315                 320

Ile Gly His Gln Asp Trp Leu Lys Gly Lys Gln Phe Thr Cys Lys Val
                325                 330                 335

Asn Asn Lys Ala Leu Pro Ser Pro Ile Glu Arg Thr Ile Ser Lys Ala
                340                 345                 350

Arg Gly Gln Ala His Gln Pro Ser Val Tyr Val Leu Pro Pro Ser Arg
            355                 360                 365

Glu Glu Leu Ser Lys Asn Thr Val Ser Leu Thr Cys Leu Ile Lys Asp
        370                 375                 380

Phe Phe Pro Pro Asp Ile Asp Val Glu Trp Gln Ser Asn Gly Gln Gln
385                 390                 395                 400

Glu Pro Glu Ser Lys Tyr Arg Thr Thr Pro Pro Gln Leu Asp Glu Asp
                405                 410                 415

Gly Ser Tyr Phe Leu Tyr Ser Lys Leu Ser Val Asp Lys Ser Arg Trp
            420                 425                 430

Gln Arg Gly Asp Thr Phe Ile Cys Ala Val Met His Glu Ala Leu His
            435                 440                 445

Asn His Tyr Thr Gln Glu Ser Leu Ser His Ser Pro Gly Lys
    450                 455                 460

<210> SEQ ID NO 23
<211> LENGTH: 1386
<212> TYPE: DNA
<213> ORGANISM: Artificial Sequence
<220> FEATURE:
<223> OTHER INFORMATION: Synthetic Construct

<400> SEQUENCE: 23
cagctgcagc tgcaggagag cggacctgga ctggtcaagc catctgaaac cctgagtctg      60
acctgtacag tgagcggcgg atctatcaac tccagctctt actattgggg ctggctgcgg     120
cagtctccag ggaaaggtct ggagtggatt gggagcttct tttacacagg ttctacttac     180
tataacccca gtctgaggtc acggctgacc atctcagtgg acacatccaa gaatcagttt     240
tccctgatgc tgagttcagt cacagccgct gatactgccg tgtactattg cgctcgacag     300
agtacctact attcggctc aggaaactat tacgggtggt tcgaccgttg ggatcagggt     360
accctggtca cagtgtccag cgcaagcacc acagcaccat ccgtgttccc cctggccccct     420 agctgcggga gtacctcagg ttccacagtc gctctggcat gtctggtgag tgggtatttc     480
cctgagccag tcaccgtgtc atggaatagc ggctctctga cttctggagt ccacaccttt     540
cctagtgtgc tgcagtctag tggcctgtac tctctgtcat ccatggtcac tgtgcccagc     600
tccaggtggc cttctgaaac tttcacctgc aacgtggccc atccagctag taagacaaaa     660
```

```
gtggacaagc ccgtgcctaa acgcgagaat ggaagagtgc cacgcccccc tgattgcccc    720
aagtgtccag ctcccgaaat gctgggggt ccttccgtgt tcatctttcc acccaagcca    780
aaagacaccc tgctgattgc aagaactcct gaggtgacct gcgtggtcgt ggacctggac    840
cccgaggacc ccgaagtcca gatttcctgg ttcgtggatg gaagcagat gcagactgcc    900 aaacccagc ccagagagga acagtttaac ggtacatatc gcgtcgtgag cgtgctgcct    960
atcggccacc aggactggct gaagggaaaa cagtttacat gcaaggtgaa caataaagct   1020
ctgccttcac caatcgagag gactatttcc aaggctcggg gacaggcaca tcagcccagc   1080
gtctatgtgc tgcctccaag tcgagaggaa ctgtcaaaga cacagtgtc cctgacttgt   1140 ctgatcaaag atttctttcc ccctgacatt gatgtggagt ggcagagcaa tggccagcag   1200
gagcctgaat ctaagtaccg cactacccca ccccagctgg acgaagatgg cagctatttc   1260
ctgtactcca agctgagcgt ggacaaatct cgatggcagc gtggagatac ctttatctgt   1320
gcagtgatgc acgaggccct gcacaatcat tacacacaag aaagtctgtc acattccccc   1380
ggcaag                                                              1386
```

<210> SEQ ID NO 24
<211> LENGTH: 217
<212> TYPE: PRT
<213> ORGANISM: Artificial Sequence
<220> FEATURE:
<223> OTHER INFORMATION: Synthetic Construct

<400> SEQUENCE: 24

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gln Gly Thr Lys Val Glu Ile Lys Arg Asn Asp Ala Gln
            100                 105                 110

Pro Ala Val Tyr Leu Phe Gln Pro Ser Pro Asp Gln Leu His Thr Gly
        115                 120                 125

Ser Ala Ser Val Val Cys Leu Leu Asn Ser Phe Tyr Pro Lys Asp Ile
    130                 135                 140

Asn Val Lys Trp Lys Val Asp Gly Val Ile Gln Asp Thr Gly Ile Gln
145                 150                 155                 160

Glu Ser Val Thr Glu Gln Asp Lys Asp Ser Thr Tyr Ser Leu Ser Ser
                165                 170                 175

Thr Leu Thr Met Ser Ser Thr Glu Tyr Leu Ser His Glu Leu Tyr Ser
            180                 185                 190

Cys Glu Ile Thr His Lys Ser Leu Pro Ser Thr Leu Ile Lys Ser Phe
        195                 200                 205

Gln Arg Ser Glu Cys Gln Arg Val Asp
    210                 215
```

<210> SEQ ID NO 25
<211> LENGTH: 651
<212> TYPE: DNA
<213> ORGANISM: Artificial Sequence
<220> FEATURE:
<223> OTHER INFORMATION: Synthetic Construct

<400> SEQUENCE: 25

```
gaaatcgtcc tgacccagtc tcccgccaca ctgagtctgt cacctggcga gagagccacc      60
ctgtcttgtc gcgcttccca gagcgtgtcc agctacctgg catggtatca gcagaagcct     120
ggacaggccc caagactgct gatctacgac gcttccaacc gagcaacagg gattccagct     180
cgtttctctg gcagtggatc agggactgac tttactctga ccatctctag tctggagccc     240
gaagatttcg ccgtgtacta ttgccagcag cggagcaact ggcccccctgc atttggtcag    300
ggcaccaagg tggaaattaa acgcaatgac gcacagcctg ccgtctacct gttccagcca     360
agtcccgatc agctgcatac aggctccgcc agcgtggtct gtctgctgaa cagctttat      420
ccaaaggaca tcaatgtgaa gtggaaagtg gacggagtca tccaggatac tgggattcag     480
gagtccgtca ccgaacagga caaagattct acatatagtc tgtcatccac actgactatg     540
agctctaccg agtacctgag tcacgaactg tattcatgcg agatcactca taagtcactg     600
cctccaccc tgattaagtc cttccagagg tctgagtgtc agcgggtgga t              651
```

<210> SEQ ID NO 26
<211> LENGTH: 457
<212> TYPE: PRT
<213> ORGANISM: Artificial Sequence
<220> FEATURE:
<223> OTHER INFORMATION: Synthetic Construct

<400> SEQUENCE: 26

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Asn Ser Ser
             20                  25                  30

Ser Tyr Tyr Trp Gly Trp Leu Arg Gln Ser Pro Gly Lys Gly Leu Glu
         35                  40                  45

Trp Ile Gly Ser Phe Phe Tyr Thr Gly Ser Thr Tyr Tyr Asn Pro Ser
     50                  55                  60

Leu Arg Ser Arg Leu Thr Ile Ser Val Asp Thr Ser Lys Asn Gln Phe
 65                  70                  75                  80

Ser Leu Met Leu Ser Ser Val Thr Ala Ala Asp Thr Ala Val Tyr Tyr
                 85                  90                  95

Cys Ala Arg Gln Ser Thr Tyr Tyr Gly Ser Gly Asn Tyr Tyr Gly
            100                 105                 110

Trp Phe Asp Arg Trp Asp Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205
```

Ile Cys Asn Val Asn His Lys Pro Ser Asn Thr Lys Val Asp Lys Arg
    210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
            260                 265                 270
Val Val Asp Val Ser His Glu Asp Pro Glu Val Lys Phe Asn Trp Tyr
        275                 280                 285
Val Asp Gly Val Glu Val His Asn Ala Lys Thr Lys Pro Arg Glu Glu
    290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Glu Glu Met
        355                 360                 365
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
        435                 440                 445
Lys Ser Leu Ser Leu Ser Pro Gly Lys
    450                 455

<210> SEQ ID NO 27
<211> LENGTH: 1371
<212> TYPE: DNA
<213> ORGANISM: Artificial Sequence
<220> FEATURE:
<223> OTHER INFORMATION: Synthetic Construct

<400> SEQUENCE: 27
cagctgcagc tgcaggagtc gggcccagga ctggtgaagc cttcggagac cctgtccctc     60
acctgcactg tctctggtgg ctccatcaac agtagtagtt actactgggg ctggctccgc    120
cagtccccag ggaaggggct ggagtggatt gggagtttct tttatactgg gagcacctac    180
tacaacccgt ccctcaggag tcgactcacc atatccgtag acacgtccaa gaaccagttc    240
tccctgatgc tgagttctgt gaccgccgca gacacggctg tatattactg tgcgagacag    300
tccacgtatt actatggttc ggggaattat tatggctggt tcgaccgctg ggaccaggga    360
accctggtca ccgtctcctc agctagcacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600

```
agcagcttgg gcacccagac ctacatctgc aacgtgaatc acaagcccag caacaccaag    660
gtggacaaga gagttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggagga gatgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta tagcaagctc   1260
accgtggaca gagcaggtg gcagcagggg aacgtcttct catgctccgt gatgcatgag   1320
gctctgcaca accactacac gcagaagagc ctctccctgt ccccgggtaa a           1371

<210> SEQ ID NO 28
<211> LENGTH: 214
<212> TYPE: PRT
<213> ORGANISM: Artificial Sequence
<220> FEATURE:
<223> OTHER INFORMATION: Synthetic Construct

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 29
<211> LENGTH: 642
<212> TYPE: DNA
<213> ORGANISM: Artificial Sequence
<220> FEATURE:
<223> OTHER INFORMATION: Synthetic Construct

<400> SEQUENCE: 29

```
gaaattgtgt tgacacagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccactgg catcccagcc       180
aggttcagtg gcagtgggtc tgggacagac ttcactctca ccatcagcag cctagagcct       240
gaagattttg cagtttatta ctgtcagcag cgtagcaact ggcctccggc gttcggccaa       300
gggaccaagg tggaaatcaa acgtacggtg gctgcaccat ctgtcttcat cttcccgcca       360
tctgatgagc agttgaaatc tggaactgcc tctgttgtgt gcctgctgaa taacttctat       420
cccagagagg ccaaagtaca gtggaaggtg gataacgccc tccaatcggg taactcccag       480
gagagtgtca cagagcagga cagcaaggac agcacctaca gcctcagcag caccctgacg       540
ctgagcaaag cagactacga gaaacacaaa gtctacgcct gcgaagtcac ccatcagggc       600
ctgagctcgc ccgtcacaaa gagcttcaac aggggagagt gt                          642
```

<210> SEQ ID NO 30
<211> LENGTH: 127
<212> TYPE: PRT
<213> ORGANISM: Artificial Sequence
<220> FEATURE:
<223> OTHER INFORMATION: Synthetic Construct

<400> SEQUENCE: 30

```
Gln Leu Gln Leu Gln Glu Ser Gly Pro Gly Leu Val Lys Pro Ser Glu
  1               5                  10                  15
Thr Leu Ser Leu Thr Cys Thr Val Ser Gly Gly Ser Ile Asn Ser Ser
             20                  25                  30
Ser Tyr Tyr Trp Gly Trp Leu Arg Gln Ser Pro Gly Lys Gly Leu Glu
         35                  40                  45
Trp Ile Gly Ser Phe Phe Tyr Thr Gly Ser Thr Tyr Tyr Asn Pro Ser
     50                  55                  60
Leu Arg Ser Arg Leu Thr Ile Ser Val Asp Thr Ser Lys Asn Gln Phe
 65                  70                  75                  80
Ser Leu Met Leu Ser Ser Val Thr Ala Ala Asp Thr Ala Val Tyr Tyr
                 85                  90                  95
Cys Ala Arg Gln Ser Thr Tyr Tyr Gly Ser Gly Asn Tyr Tyr Gly
            100                 105                 110
Trp Phe Asp Arg Trp Asp Gln Gly Thr Leu Val Thr Val Ser Ser
            115                 120                 125
```

<210> SEQ ID NO 31
<211> LENGTH: 381
<212> TYPE: DNA
<213> ORGANISM: Artificial Sequence
<220> FEATURE:
<223> OTHER INFORMATION: Synthetic Construct

<400> SEQUENCE: 31

```
cagctgcagc tgcaggagtc gggcccagga ctggtgaagc cttcggagac cctgtccctc        60
acctgcactg tctctggtgg ctccatcaac agtagtagtt actactgggg ctggctccgc       120
```

```
cagtccccag ggaaggggct ggagtggatt gggagtttct tttatactgg gagcacctac    180
tacaacccgt ccctcaggag tcgactcacc atatccgtag acacgtccaa gaaccagttc    240
tccctgatgc tgagttctgt gaccgccgca gacacggctg tatattactg tgcgagacag    300
tccacgtatt actatggttc ggggaattat tatggctggt tcgaccgctg ggaccaggga    360
accctggtca ccgtctcctc a                                              381
```

```
<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Phe Gly Gln Gly Thr Lys Val Glu Ile Lys
            100                 105

```
<210> SEQ ID NO 33
<211> LENGTH: 321
<212> TYPE: DNA
<213> ORGANISM: Artificial Sequence
<220> FEATURE:
<223> OTHER INFORMATION: Synthetic Construct

<400> SEQUENCE: 33
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggcctccggc gttcggccaa    300
gggaccaagg tggaaatcaa a                                              321
```

```
<210> SEQ ID NO 34
<211> LENGTH: 15
<212> TYPE: PRT
<213> ORGANISM: Artificial Sequence
<220> FEATURE:
<223> OTHER INFORMATION: Synthetic Construct

<400> SEQUENCE: 34
```

Thr Val Ser Gly Gly Ser Ile Asn Ser Ser Ser Tyr Tyr Trp Gly
1               5                   10                  15

```
<210> SEQ ID NO 35
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 35

Ser Phe Phe Tyr Thr Gly Ser Thr Tyr Tyr Asn Pro Ser Leu Arg Ser
1               5                   10                  15

<210> SEQ ID NO 36
<211> LENGTH: 19
<212> TYPE: PRT
<213> ORGANISM: Artificial Sequence
<220> FEATURE:
<223> OTHER INFORMATION: Synthetic Construct

<400> SEQUENCE: 36

Ala Arg Gln Ser Thr Tyr Tyr Tyr Gly Ser Gly Asn Tyr Tyr Gly Trp
1               5                   10                  15

Phe Asp Arg

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

Arg Ala Ser Gln Ser Val Ser Ser Tyr Leu Ala
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Tyr Asp Ala Ser Asn Arg Ala Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Gln Gln Arg Ser Asn Trp Pro Pro Ala
1               5
```

ANTI-CANINE PLATELET DERIVED GROWTH FACTOR RECEPTOR ALPHA ANTIBODY

The present application is a national phase entry under 35 U.S.C. § 371 of International Patent Application PCT/US2017/042996, filed on Jul. 20, 2017 and published in English as International Patent Publication WO2018/022407A1 on Feb. 1, 2018, which claims benefit of priority to U.S. Pat. App. Ser. No. 62/367,808 filed Jul. 28, 2016; all of which are incorporated by reference in their entirety.

The present invention is directed towards the field of immunology and the treatment of cancer. More specifically, the present invention relates to anti-canine platelet derived growth factor receptor alpha (cPDGFRA) antibodies to the cPDGFRA and methods of use to treat certain disorders such as osteosarcoma (OSA) in dogs.

Sarcomas are a diverse and relatively rare type of cancer that usually develop in the connective tissue of the body, which include fat, blood vessels, nerves, bones, muscles, deep skin tissues and cartilage. OSA represents about 5% of all cancers in dogs, but is the most common form of canine bone tumor. OSA most often occurs in large and giant breed dogs, typically in middle aged or elderly animals. It is considered a highly aggressive form of cancer and over 90% of clinically significant cases have already micro-metastasized by the time of diagnosis. In dogs, treatment options include radiation and/or chemotherapy, and amputation of the limb. Median survival time with various chemotherapy regimens is about one year, while survival with amputation alone is about three months. Unfortunately, an effective treatment for canine osteosarcoma still remains elusive and there exists a need for more and different therapies that may prove to be effective in treating them.

PDGFRA is a tyrosine kinase receptor that is overexpressed in 70-80% of human OSAs and it may be a suitable target for anti-PDGFRA monoclonal antibody therapy. Because canine OSA shows histopathological and clinical features similar to human OSA, cPDGFRA may also be a suitable therapeutic target for OSA in dogs. It has been demonstrated in immunohistochemical (IHC) studies that cPDGFRA is expressed in 78% of evaluated cases. Further, its ligand canine PDGFA was shown to be expressed in 42% of cases (Maniscalco, et al. *Vet J.* 2013. 195:41).

Olaratumab (also referred to as IMC-3G3) is a fully human IgG1 monoclonal antibody directed against human PDGFRA with potential antineoplastic activity. Successful treatment of soft tissue sarcomas by using Olaratumab can be found in International Publication No. WO2016/003789, for example. Olaratumab selectively binds to human PDGFRA, blocking the binding of its ligand, PDGF. Signal transduction downstream of PDGFR through the MAPK and PI3K pathways is inhibited, which may result in inhibition of angiogenesis and tumor cell proliferation.

Given that Olaratumab is a fully human monoclonal antibody, chronic administration of Olaratumab, or any other fully human antibody, in dogs would likely elicit the development of anti-drug antibodies leading to increasingly strong immune responses after each subsequent treatment of the canine patient with Olaratumab.

Accordingly, the present invention provides a monoclonal antibody that binds canine platelet derived growth factor receptor alpha (cPDGFRA) and has a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein the amino acid sequence of LCDR1 is given by SEQ ID NO:16, the amino acid sequence of LCDR2 is given by SEQ ID NO: 18, the amino acid sequence of LCDR3 is given by SEQ ID NO: 20, the amino acid sequence of HCDR1 is given by SEQ ID NO: 6, the amino acid sequence of HCDR2 is given by SEQ ID NO: 8, and the amino acid sequence of HCDR3 is given by SEQ ID NO: 10.

In another aspect, the present invention provides a monoclonal antibody having a light chain variable region (LCVR) and a heavy chain variable region (HCVR), wherein the amino acid sequence of the LCVR is given by SEQ ID NO: 14 and the amino acid sequence of the HCVR is given by SEQ ID NO: 4.

In yet another aspect, the present invention provides a monoclonal antibody having a light chain (LC) and a heavy chain (HC), wherein the amino acid sequence of the LC is given by SEQ ID NO: 12 and the amino acid sequence of the HC is given by SEQ ID NO: 1.

In an aspect the present invention discloses anti-cPDGFRA antibodies for use in therapy.

In another aspect the present invention discloses anti-cPDGFRA antibodies for use in the treatment of osteosarcoma in a canine patient.

In yet another aspect, the present invention further relates to the use of an antibody of the invention in the manufacture of a medicament for the treatment of osteosarcoma in a canine patient.

Unless indicated otherwise, the term "antibody" (Ab) refers to an immunoglobulin molecule comprising two heavy chains (HC) and two light chains (LC) interconnected by disulfide bonds. The amino terminal portion of each chain includes a variable region of about 100 to about 110 amino acids primarily responsible for antigen recognition via the complementarity determining regions (CDRs) contained therein. The carboxy-terminal portion of each chain defines a constant region primarily responsible for effector function.

As used herein, the terms "complementarity determining region" and "CDR", refer to the non-contiguous antigen combining sites found within the variable region of LC and HC polypeptides of an antibody or an antigen-binding fragment thereof.

As used herein, the term "light chain variable region" (LCVR) refers to a portion of a LC of an antibody molecule that includes amino acid sequences of Complementarity Determining Regions (CDRs; i.e., LCDR1, LCDR2, and LCDR3), and Light Framework Regions (LFRWs).

As used herein, the term "heavy chain variable region (HCVR)" refers to a portion of a HC of an antibody molecule that includes amino acid sequences of Complementarity Determining Regions (CDRs; i.e., HCDR1, HCDR2, and HCDR3), and Heavy Framework Regions (HFRWs).

The CDRs are interspersed with regions that are more conserved, termed framework regions ("FRW"). Each LCVR and HCVR is composed of three CDRs and four FRWs, arranged from amino-terminus to carboxy-terminus in the following order: FRW1, CDR1, FRW2, CDR2, FRW3, CDR3, FRW4. The three CDRs of the light chain are referred to as "LCDR1, LCDR2, and LCDR3" and the three CDRs of the HC are referred to as "HCDR1, HCDR2, and HCDR3." The CDRs contain most of the residues which form specific interactions with the antigen. The numbering and positioning of CDR amino acid residues within the LCVR and HCVR regions is in accordance with known conventions (e.g., Kabat (1991), Chothia (1987), and/or North (2011)). In different embodiments of the invention, the FRWs of the antibody may be identical to the germline sequences, or may be naturally or artificially modified.

In certain embodiments, the anti-cPDGFRA Ab of the present invention is altered to increase or decrease the extent to which the antibody is glycosylated. Addition or deletion of glycosylation sites to an antibody may be conveniently accomplished by altering the amino acid sequence such that one or more glycosylation sites is created or removed.

As used herein, the term "Olaratumab" refers to a fully human IgG1 monoclonal antibody directed against human PDGFR, human PDGFRA, and/or human PDGFRA/PDG-FRB heterodimers. Olaratumab may also be referred to herein as "human Olaratumab". As used herein, the HC amino acid sequence of Olaratumab is represented by SEQ ID NO. 26, and the LC amino acid sequence of Olaratumab is represented by SEQ ID NO. 28. The nucleotide sequences that encode the HC and LC amino acid sequences of Olaratumab are SEQ ID NO. 27 and SEQ ID NO. 28, respectively.

As used herein, the term "kit" refers to a package comprising at least two separate containers, wherein a first container contains a K9-6N6.2 Ab and a second container contains pharmaceutically acceptable carriers, diluents, or excipients. As used herein, the term "kit" also refers to a package comprising at least two separate containers, wherein a first container contains K9-6N6.2 Ab, and another antibody preferably for the treatment of cancers other than lymphomas. A "kit" may also include instructions to administer all or a portion of the contents of these first and second containers to a cancer patient. Optionally, these kits also include a third container containing a composition comprising a known chemotherapeutic agent.

As used herein, the terms "treating," "to treat," or "treatment" refers to restraining, slowing, stopping, reducing, or reversing the progression or severity of an existing symptom, disorder, condition, or disease.

As used herein, the term "effective amount" refers to the amount or dose of an anti-cPDGFRA Ab which, upon single or multiple dose administration to the patient, provides an effective response in the patient under diagnosis or treatment.

An effective amount can be readily determined by the use of known techniques and by observing results obtained under analogous circumstances. In determining the effective amount for a patient, a number of factors are considered, including, but not limited to: the species or breed of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

AN ANTI-CPDGFRA ANTIBODY

An anti-cPDGFRA antibody designated K9-6N6.1 was created by cloning the entire HCVR of Olaratumab (SEQ ID NO: 31) in frame to the canine IgB heavy chain constant region (GENBANK: AAL35302) to generate a single cDNA sequence (SEQ ID NO: 23). Additionally, the entire LCVR (SEQ ID NO: 33) of Olaratumab was cloned in frame to the canine Kappa light chain constant region (GENBANK: E02906.1) to generate a single cDNA sequence (SEQ ID NO: 25).

K9-6N6.1 contains variable regions identical to those of the fully human Olaratumab. As depicted in Table 1, Olaratumab and K9-6N6.1 binds to cPDGFRA with an affinity that is about 10 fold lower than that of Olaratumab binding to human PDGFRA.

TABLE 1

Cross-species binding affinity of human and K9-6N6.1 parental anti-cPDGFRA antibodies

| Antibody (30 nM) | PDGFRA-Fc | $K_{on}$ (1/Ms) | $K_{off}$ (1/s) | $K_D$ (M) |
|---|---|---|---|---|
| Olaratumab | Human | 8.08E+05 | 2.48E−04 | 3.07E−10 |
| Olaratumab | Dog | 8.56E+05 | 2.94E−03 | 3.44E−09 |
| K9-6N6.1 | Dog | 8.40E+05 | 1.61E−03 | 1.92E−09 |

High Throughput Mutagenesis

Mutagenesis experiments were performed to generate antibodies derived from K9-6N6.1. Mutagenic oligonucleotides were generated using an Excel design template (5' truncation) in a 96-well format and ordered from Integrated DNA Technologies. Mutagenesis was performed using an optimized Quick Change reaction protocol. Briefly, each well (mutagenesis reaction) of a 96-well plate contained enzymatically digested vector DNA for the expression of HC or LC of K9-6N6.1, KOD Hotstart Polymerase, MgSO₄, dNTP and different primers for the generation of single mutations. The plate was placed into a PCR machine with the following program: 95° C. for 2 minutes, followed by 20 cycles at 95° C., 20 sec; 60° C., 10 sec; 68° C., 4 min, and then a final extension at 68° C. for 5 minutes. After PCR, 2 µl of DpnI restriction enzyme and reaction buffer were added to the PCR reaction and incubated at 37° C. for 16 hours, followed by incubation at 70° C. for 30 min to inactivate the DpnI. One µl of DNA was then transformed into 10G chemically competent bacterial cells (Lucigen). DNA from the 96-well plate was prepared using a Qiagen 96-well DNA preparation kit, and subjected to DNA sequence analysis.

A total of 210 single point mutations were generated. The efficiency of mutagenesis was monitored by DNA sequence analysis on randomly selected wells. Among 23 wells selected, 3 wells (13%) had a rate of incorporation of the desired mutation below 75% (37-65%). The rest of wells showed incorporation rates of the desired mutations from 75 to 100%.

Deep-Well Expression of Single Mutants and Pools

DNA was prepared from bacteria transformed with either pooled mutagenesis reactions or DNA from single clones confirmed by sequence analysis. Bacterial cells were inoculated and propagated overnight. DNA was prepared using DirectPrep 96 MiniPrep Kit (Qiagen, cat#27361) following the manufacturer's instructions. Following sequence confirmation, DNA from pools or single clones was used to co-transfect Expi293 cells with the HC or LC from the parental K9-6N6.1. Expression of the resulting IgG molecules was conducted in deep-well plates.

PhyNexus Tip Enrichment

Six days after the transfection and subsequent cell growth, supernatants of the cell cultures were collected. Antibodies in culture supernatants were enriched with PhyNexus ProA Phytip columns using a BioMek automated liquid handling system. Antibody supernatants were loaded in the columns and captured on Protein A resin. After washing twice with PBS, antibodies were eluted from the column with 90 µl of 0.1M Glycine-HCl (pH 2.7), and neutralized with 10 µl of Tris-HCl buffer (pH8.0). Antibody concentrations were determined by Octet on a ProA sensor using an antibody standard of known concentration.

Preliminary Screening

All 210 mutants from the pooled transfection and the parental K9-6N6.1 were assessed for binding and blocking using single point ELISAs. Some of the enriched variants from the pooled mutagenesis demonstrated increased binding and blocking activity, while others showed reduced binding to cPDGFRA compared to the parental K9-6N6.1. From the variants showing improved interaction with the dog receptor, 54 clones were selected for further evaluation using titration assays for binding and blocking.

Confirmation of Binding and Blocking Activity

In the assessment of binding, serially diluted K9-6N6.1 variants (enriched or purified) and the parental antibody were added to plates coated with cPDGFRA-Fc (100 µl at 0.5 µg/ml), and incubated at room temperature for 1 hour. To evaluate blockade of the interaction with ligand, serially diluted variants of K9-6N6.1 (enriched and purified) and the parental K9-6N6.1 antibody were mixed with a fixed amount of biotinylated-cPDGFRA (0.0625 μg/ml) and incubated at room temperature for 1 hour. The mixture was transferred to 96-well plates pre-coated with canine PDGFAA (0.125 μg/ml) and incubated at room temperature for 2 hours. The plates were then washed, detection antibodies were added, and the amount of binding determined as described above.

For assessment of binding and blocking using Olaratumab, the above methods were modified. In the binding ELISA, plates were coated with 100 μl of human PDGFRA at 1 μg/ml, and HRP-Protein L (GenScript) was used for detection. In the blocking assay, 0.5 μg/ml human PDGFRA and 0.5 μg/ml of PDGFAA were used. Plate bound human PDGFRA was detected with a biotinylated anti-human PDGFRA antibody (R&D).

Screening of Mutants Using Binding and Blocking Assays (Single Point ELISA)

Variants from the mutagenesis were initially screened using a single-point ELISA. In the binding assay, 0.5 μg/ml of enriched antibody, either variants of K9-6N6.1 or the parental K9-6N6.1 antibody were added to plates coated with cPDGFRA (100 μl at 0.5 μg/ml) and incubated at room temperature for 1 hour. The plates were washed three times with phosphate buffered saline with Tween® (PBST), and then incubated at room temperature for an additional hour with a goat anti-canine-Fab antibody/horse radish peroxidase (HRP) conjugate (Sigma). After washing three times with PBST, tetramethylbenzidine (TMB) peroxidase substrate was added to the plate. The absorbance at 450 nm was read using a microplate reader.

In the blocking assay, 15 μg/ml of the enriched variants or the parental antibody were first mixed with a fixed amount of biotinylated-cPDGFRA (0.0625 μg/ml) and incubated at room temperature for 1 hour. The mixture was transferred to 96-well plates pre-coated with canine PDGFAA (0.125 μg/ml) and incubated at room temperature for 2 hours. After washing three times with PBST, the plates were incubated with HRP-conjugated streptavidin for 1 hour. The plates were then washed and developed as described above.

Identification of Beneficial Mutations

Results of binding and blocking were analyzed and EC50 (binding) and IC50 (blocking) values were calculated. To estimate improvement of each mutant variant over the parental K9-6N6.1 molecule, fold improvement was calculated as parental EC50 or IC50 divided by variant EC50 or IC50.

As depicted in Table 2, among the variants, HC-Y100D (clone 1F12) showed an almost 17-fold improvement in blocking the binding of canine PDGF-AA to cPDGFRA, but binding was not detected to human PDGFRA. However, a mutation in the LC, S28A (2A2), showed 13-fold improvement in blocking activity compared with the parental antibody, while retaining binding to both human PDGFRA and cPDGFRA. LC-S28A (clone 2A2) is a mutation that improves binding to PDGFRA. The unexpected improvement in binding and blocking activities of HC-Y100D (1F12) and LC-S28A (2A2) were confirmed by using single clones.

TABLE 2

Characterization of selected affinity variants for PDGFRA binding and blocking activity

| Pool evaluation | LC | HCDR3 |
|---|---|---|
| Clone name | 2A2 | 1F12 |
| Beneficial mutation | S28A | Y100D |
| cPDGFRA Binding EC50 improvement (fold) | 1.43 | 1.58 |
| cPDGFRA Blocking IC50 improvement (fold) | 13.41 | 16.86 |
| Human PDGFRA Binding EC50 improvement (fold) | 1.83 | not detected |

Combination of HC-Y100D and LC-S28A

Heavy and light chains of the K9-6N6.1 variants HC-Y100D and LC-S28A were co-expressed to determine the impact on binding and blocking of combining the two mutations. Briefly, the HC expression vector with HC-Y100D (1F12) was co-transfected into HEK293 cells with the LC expression vector containing the S28A (2A2) mutation. Protein was purified with using a ProA column and evaluated in binding and blocking assays. The IC50 of the HC-Y100D and LC-S28A (clone 1F12-2A2) combination antibody indicated an additional two fold improvement over 1F12.

Evaluation of Affinity

The binding kinetics of selected K9-6N6.1 variants to cPDGFRA were measured using a BIAcore T200 instrument (BIAcore, Inc., Piscataway, N.J.). Briefly, a cPDGFRA extracellular domain (ECD)-Fc fusion protein was immobilized on a sensor chip and antibody was injected at various concentrations. Sensograms were obtained at each concentration and evaluated using the BIA Evaluation 3.0 program to determine rate constants. The affinity constant (KD) was calculated from the ratio of rate constants Koff/Kon. The evaluation was performed at 25° C. As depicted in Table 3, kinetic evaluation showed that overall affinities are improved over parent K9-6N6.1, 5-fold for 1F12 (Y100D) and 12-fold for 1F12-2A2 (Y100D and S28A).

TABLE 3

Surface Plasmon Resonance (SPR) binding affinity of parent K9-6N6.1 and affinity enhanced variants to canine PDGFRA

| Binding to cPDGFRA-ECD-Xa-Fc | Kon (1/Ms) | Koff (1/s) | KD (M) | Improvement (fold) |
|---|---|---|---|---|
| K9-6N6.1 | 5.08E+05 | 2.47E−03 | 4.87E−09 | 1 |
| 1F12 | 4.53E+05 | 4.29E−04 | 9.46E−10 | 5 |
| 1F12-2A2 | 5.07E+05 | 2.03E−04 | 4.01E−10 | 12 |

Removal of Deamidation Site in K9-6N6.1

The amino acid sequence of the IgG-B portion of K9-6N6.1 contains an asparagine residue at position 232 is followed by glycine, a small, flexible residue (G233). The NG pairing in exposed regions of proteins often yields high levels of deamidation. Biophysical evaluation of K9-6N6.1 revealed that about twenty percent of the generated antibody was undergoing deamidation of N232 (asparagine 232) in the hinge region of the antibody.

To eliminate the occurrence of deamidation of K9-6N6.1, site-directed mutagenesis was used to replace N232 with aspartic acid (D), serine (S), or glutamine (Q). The substitutions were based on similarity of the side chain to that of asparagine and included consideration of size, polarity, and type. A standard mutagenesis protocol was used. Mutations were confirmed by DNA sequencing. Mutated antibodies were expressed using transiently transfected HEK293 cells and purified with protein A columns. Purified proteins were then evaluated using binding and blocking assays (ELISA) and the results were compared to the parental K9-6N6.1 as a control.

Selection of N232S

As depicted in Table 4, all three N232 variants retained the binding and blocking activity of the parental K9-6N6.1, with EC50 values ranging from 0.19 to 0.21 nM and IC50 values from 27 to 36 nM. In addition, qPCR (quantitative polymerase chain reaction) was used to assess the thermostability of the mutated antibodies. The results showed that the thermostability of all three variants was unchanged relative to the parental K9-6N6.1. Serine is less likely to undergo post-translational modification than aspartic acid and glutamine. Serine was selected as the replacement for asparagine at position 232.

TABLE 4

Characterization of deamidation variants of K9-6N6.1

| | Binding (EC$_{50}$) | Blocking (IC$_{50}$) | Tm (° C. from qPCR) |
|---|---|---|---|
| N232D | 0.209 | 32.06 | 59.4 |
| N232S | 0.195 | 27.81 | 59.6 |
| N232Q | 0.215 | 36.27 | 59.6 |
| Parental K9-6N6.1 | 0.272 | 31.51 | 59.4 |

Removal of N-Linked Glycosylation Site in K9-6N6.1

Mammalian cells are capable of generating post-translational modifications to antibodies, this includes glycosylation, typically at N or O-linked sites. The sequence N-x-S/T is often a site at which glycosylation occurs through post-translational modification. For monoclonal antibodies, there is typically only a single N-linked site within the CH2 region of the heavy chain constant region (typically at N297 for human IgGs). For monoclonal antibodies the presence and content of this N-linked glycosylation may contribute to its ability to bind to Fc receptors and mediate immune effector function. As a result of the production process in cultured cells, the extent and content of glycans added to N-linked sites can vary, and contribute to the heterogeneity, and potential activity (if effector function is important) of the product.

Depending on its location within a CDR sequence and the extent of glycosylation, the presence of additional N-linked sites within variable regions of monoclonal antibodies may impact its potency and can also contribute to product heterogeneity during manufacture. Depending on the host cell used for production (e.g. mouse NSO cells), these "Fab" or V-region glycosylation sites may be preferentially glycosylated with atypical glycans which can elicit an immune hypersensitivity response.

For replacement of N-linked sites, Q (glutamine) is typically used as a conservative amino acid substitution that removes the consensus sequence for glycosylation. Thus, using standard mutagenesis techniques, a N30Q residue substitution was made within the HCDR1 of K9-6N6.1. The N30Q substitution did not substantially affect the binding to receptor as compared to the parental K9-6N6.1.

K9-6N6.2 Sequence

K9-6N6.2 is derived from K9-6N6.1. K9-6N6.2 contains two substitutions to the K9-6N6.1 parent molecule, VH-Y100D and VL-S28A, that improve affinity, as well as two substitutions, N30Q and N232S, that add stability and result in fewer post translational modifications than in the K9-6N6.1 parent antibody.

SEQ ID NO: 1 is the amino acid sequence of the HC of K9-6N6.2.

SEQ ID NO: 2 corresponds to the nucleotide sequence that encodes for the amino acid sequence corresponding to SEQ ID NO: 1 and also contains a DNA coding sequence for a murine heavy chain leader, as well as DNA coding sequences for restriction enzymes HindIII and EcoRI.

SEQ ID NO: 3 is the translated amino acid sequence of SEQ ID NO: 2 and contains the HC of K9-6N6.2.

SEQ ID NO: 4 is the amino acid sequence of the HCVR of K9-6N6.2.

SEQ ID NO: 5 is the nucleotide sequence encoding the HCVR of K9-6N6.2.

SEQ ID NO: 6 is the heavy chain CDR1 amino acid sequence of K9-6N6.2.

SEQ ID NO: 7 is the nucleotide sequence encoding the HCDR1 amino acid sequence of K9-6N6.2.

SEQ ID NO: 8 is the HCDR2 amino acid sequence of K9-6N6.2.

SEQ ID NO: 9 is the nucleotide sequence encoding the HCDR2 amino acid sequence of K9-6N6.2.

SEQ ID NO: 10 is the HCDR3 amino acid sequence of K9-6N6.2.

SEQ ID NO: 11 is the nucleotide sequence encoding the HCDR3 amino acid sequence of K9-6N6.2.

SEQ ID NO: 12 is the LC amino acid sequence of K9-6N6.2.

SEQ ID NO: 13 is the nucleotide sequence encoding the LC of K9-6N6.2.

SEQ ID NO: 14 is the amino acid sequence of the LCVR of K9-6N6.2.

SEQ ID NO: 15 is the nucleotide sequence encoding the LCVR of K9-6N6.2.

SEQ ID NO: 16 is the LCDR1 amino acid sequence of K9-6N6.2.

SEQ ID NO: 17 is the nucleotide sequence encoding the LCDR1 amino acid sequence of K9-6N6.2.

SEQ ID NO: 18 is the LCDR2 amino acid sequence of K9-6N6.2.

SEQ ID NO: 19 is the nucleotide sequence encoding the LCDR2 amino acid sequence of K9-6N6.2.

SEQ ID NO: 20 is the LCDR3 amino acid sequence of K9-6N6.2.

SEQ ID NO: 21 is the nucleotide sequence encoding the LCDR3 amino acid sequence of K9-6N6.2.

SEQ ID NO: 22 is the HC amino acid sequence of K9-6N6.1.

SEQ ID NO: 23 is the nucleotide sequence encoding the HC amino acid sequence of K9-6N6.1.

SEQ ID NO: 24 is the LC amino acid sequence of K9-6N6.1.

SEQ ID NO: 25 is the nucleotide sequence encoding the LC amino acid sequence of K9-6N6.1.

SEQ ID NO: 26 is the HC amino acid sequence of Olaratumab.

SEQ ID NO: 27 is the nucleotide sequence encoding the HC amino acid sequence of Olaratumab.

SEQ ID NO: 28 is the LC amino acid sequence of Olaratumab.

SEQ ID NO: 29 is the nucleotide sequence encoding the LC amino acid sequence of Olaratumab.

SEQ ID NO: 30 is the HCVR amino acid sequence of Olaratumab.

SEQ ID NO: 31 is the nucleotide sequence encoding the HCVR amino acid sequence of Olaratumab.

SEQ ID NO: 32 is the LCVR amino acid sequence of Olaratumab.

SEQ ID NO: 33 is the nucleotide sequence encoding the LCVR amino acid sequence of Olaratumab.

SEQ ID NO: 34 is the HCDR1 amino acid sequence of Olaratumab.

SEQ ID NO: 35 is the HCDR2 amino acid sequence of Olaratumab.

SEQ ID NO: 36 is the HCDR3 amino acid sequence of Olaratumab.

SEQ ID NO: 37 is the LCDR1 amino acid sequence of Olaratumab.

SEQ ID NO: 38 is the LCDR2 amino acid sequence of Olaratumab.

SEQ ID NO: 39 is the LCDR3 amino acid sequence of Olaratumab.

Method for Making K9-6N6.2

K9-6N6.2 was engineered for expression utilizing glutamine synthetase (GS) expression plasmids for use in mammalian cells. The cDNAs encoding the heavy and the light chains were cloned into expression cassettes regulated by the viral CMV promoter and SV40 transcriptional terminator and polyadenylation 3' UTR. Both cassettes were contained on a single plasmid, along with an expression cassette for the selectable GS marker. For K9-6N6.2, the expression plasmid was first evaluated in transient expression in CHO cells utilizing a lipid-based transfection process (ExpiCHO; ThermoFisher). For cell line generation, CHO cells were electroporated with the K9-6N6.v2 expression vector and clones selected in media lacking glutamine in the presence of the inhibitor methionine sulfoximine. Following clone selection, cell lines were evaluated for production titer, with clones reaching 1 g/L or higher selected for production. The selected production line was expanded and a frozen cell bank established for production of the monoclonal antibody K9-6N6.2. For material produced from transient or stable transfection, K9-6N6.2 was purified by Pro-A affinity chromatography.

SEQUENCES

SEQ ID NO: 1 is the amino acid sequence of the heavy chain of K9-6N6.2.

QLQLQESGPGLVKPSETLSLTCTVSGGSIQSSSYYWGWLRQSPGKGLEWI

GSFFYTGSTYYNPSLRSRLTISVDTSKNQFSLMLSSVTAADTAVYYCARQ

STYYDGSGNYYGWFDRWDQGTLVTVSSASTTAPSVFPLAPSCGSTSGSTV

-continued
ALACLVSGYFPEPVTVSWNSGSLTSGVHTFPSVLQSSGLYSLSSMVTVPS

SRWPSETFTCNVAHPASKTKVDKPVPKRESGRVPRPPDCPKCPAPEMLGG

PSVFIFPPKPKDTLLIARTPEVTCVVVDLDPEDPEVQISWFVDGKQMQTA

KTQPREEQFNGTYRVVSVLPIGHQDWLKGKQFTCKVNNKALPSPIERTIS

KARGQAHQPSVYVLPPSREELSKNTVSLTCLIKDFFPPDIDVEWQSNGQQ

EPESKYRTTPPQLDEDGSYFLYSKLSVDKSRWQRGDTFI

SEQ ID NO: 2 is the nucleotide sequence that encodes for the amino acid sequence corresponding to SEQ ID NO: 1 and also contains a DNA coding sequence for a murine heavy chain leader, as well as DNA coding sequences for restriction enzymes HindIII and EcoRI.

AAGCTTGCCGCCACCATGGGCTGGTCTTGCATCATTCTGTTCCTGGTCGC

AACAGCCACTGGAGTGCACTCCCAGCTGCAGCTGCAGGAGAGCGGACCTG

GACTGGTCAAGCCATCTGAAACCCTGAGTCTGACCTGTACAGTGAGCGGC

GGATCTATCCAGTCCAGCTCTTACTATTGGGGCTGGCTGCGGCAGTCTCC

AGGGAAAGGTCTGGAGTGGATTGGGAGCTTCTTTTACACAGGTTCTACTT

ACTATAACCCCAGTCTGAGGTCACGGCTGACCATCTCAGTGGACACATCC

AAGAATCAGTTTTCCCTGATGCTGAGTTCAGTCACAGCCGCTGATACTGC

CGTGTACTATTGCGCTCGACAGAGTACCTACTATGACGGCTCAGGAAACT

ATTACGGGTGGTTCGACCGTTGGGATCAGGGTACCCTGGTCACAGTGTCC

AGCGCAAGCACCACAGCACCATCCGTGTTCCCCCTGGCCCCTAGCTGCGG

GAGTACCTCAGGTTCCACAGTCGCTCTGGCATGTCTGGTGAGTGGGTATT

TCCCTGAGCCAGTCACCGTGTCATGGAATAGCGGCTCTCTGACTTCTGGA

GTCCACACCTTTCCTAGTGTGCTGCAGTCTAGTGGCCTGTACTCTCTGTC

ATCCATGGTCACTGTGCCCAGCTCCAGGTGGCCTTCTGAAACTTTCACCT

GCAACGTGGCCCATCCAGCTAGTAAGACAAAAGTGGACAAGCCCGTGCCT

AAACGCGAGAGTGGAAGAGTGCCACGCCCCCCTGATTGCCCCAAGTGTCC

AGCTCCCGAAATGCTGGGGGGTCCTTCCGTGTTCATCTTTCCACCCAAGC

CAAAAGACACCCTGCTGATTGCAAGAACTCCTGAGGTGACCTGCGTGGTC

GTGGACCTGGACCCCGAGGACCCCGAAGTCCAGATTTCCTGGTTCGTGGA

TGGGAAGCAGATGCAGACTGCCAAAACCCAGCCCAGAGAGGAACAGTTTA

ACGGTACATATCGCGTCGTGAGCGTGCTGCCTATCGGCCACCAGGACTGG

CTGAAGGGAAAACAGTTTACATGCAAGGTGAACAATAAAGCTCTGCCTTC

ACCAATCGAGAGGACTATTTCCAAGGCTCGGGGACAGGCACATCAGCCCA

GCGTCTATGTGCTGCCTCCAAGTCGAGAGGAACTGTCAAAGAACACAGTG

TCCCTGACTTGTCTGATCAAAGATTTCTTTCCCCCTGACATTGATGTGGA

GTGGCAGAGCAATGGCCAGCAGGAGCCTGAATCTAAGTACCGCACTACCC

CACCCCAGCTGGACGAAGATGGCAGCTATTTCCTGTACTCCAAGCTGAGC

GTGGACAAATCTCGATGGCAGCGTGGAGATACCTTTATCTGTGCAGTGAT

GCACGAGGCCCTGCACAATCATTACACACAAGAAAGTCTGTCACATTCCC

CCGGCAAGTGAGAATTC

SEQ ID NO: 3 is the translated amino acid sequence of SEQ ID NO: 2 and contains the heavy chain of K9-6N6.2.

QLQLQESGPGLVKPSETLSLTCTVSGGSIQSSSYYWGWLRQSPGKGLEWI
GSFFYTGSTYYNPSLRSRLTISVDTSKNQFSLMLSSVTAADTAVYYCARQ
STYYDGSGNYYGWFDRWDQGTLVTVSSASTTAPSVFPLAPSCGSTSGSTV
ALACLVSGYFPEPVTVSWNSGSLTSGVHTFPSVLQSSGLYSLSSMVTVPS
SRWPSETFTCNVAHPASKTKVDKPVPKRESGRVPRPPDCPKCPAPEMLGG
PSVFIFPPKPKDTLLIARTPEVTCVVVDLDPEDPEVQISWFVDGKQMQTA
KTQPREEQFNGTYRVVSVLPIGHQDWLKGKQFTCKVNNKALPSPIERTIS
KARGQAHQPSVYVLPPSREELSKNTVSLTCLIKDFFPPDIDVEWQSNGQQ
EPESKYRTTPPQLDEDGSYFLYSKLSVDKSRWQRGDTFICAVMHEALHNH
YTQESLSHSPGK

SEQ ID NO: 4 is the amino acid sequence of the heavy chain variable region of K9-6N6.2.

QLQLQESGPGLVKPSETLSLTCTVSGGSIQSSSYYWGWLRQSPGKGLEWI
GSFFYTGSTYYNPSLRSRLTISVDTSKNQFSLMLSSVTAADTAVYYCARQ
STYYDGSGNYYGWFDRWDQGTLVTVSS

SEQ ID NO: 5 is the nucleotide sequence encoding the heavy chain variable region of K9-6N6.2.

CAGCTGCAGCTGCAGGAGAGCGGACCTGGACTGGTCAAGCCATCTGAAAC
CCTGAGTCTGACCTGTACAGTGAGCGGCGGATCTATCCAGTCCAGCTCTT
ACTATTGGGCTGGCTGCGGCAGTCTCCAGGGAAAGGTCTGGAGTGGATT
GGGAGCTTCTTTTACACAGGTTCTACTTACTATAACCCCAGTCTGAGGTC
ACGGCTGACCATCTCAGTGGACACATCCAAGAATCAGTTTTCCCTGATGC
TGAGTTCAGTCACAGCCGCTGATACTGCCGTGTACTATTGCGCTCGACAG
AGTACCTACTATGACGGCTCAGGAAACTATTACGGGTGGTTCGACCGTTG
GGATCAGGGTACCCTGGTCACAGTGTCCAGC

SEQ ID NO: 6 is the heavy chain CDR1 amino acid sequence of K9-6N6.2.

TVSGGSIQSSSYYWG

SEQ ID NO: 7 is the nucleotide sequence encoding the heavy chain CDR1 amino acid sequence of K9-6N6.2.

ACAGTGAGCGGCGGATCTATCCAGTCCAGCTCTTACTATTGGGGC

SEQ ID NO: 8 is the heavy chain CDR2 amino acid sequence of K9-6N6.2.

SFFYTGSTYYNPSLRS

SEQ ID NO: 9 is the nucleotide sequence encoding the heavy chain CDR2 amino acid sequence of K9-6N6.2.

AGCTTCTTTTACACAGGTTCTACTTACTATAACCCCAGTCTGAGGTCA

SEQ ID NO: 10 is the heavy chain CDR3 amino acid sequence of K9-6N6.2.

ARQSTYYDGSGNYYGWFDR

SEQ ID NO: 11 is the nucleotide sequence encoding the heavy chain CDR3 amino acid sequence of K9-6N6.2.

GCTCGACAGAGTACCTACTATGACGGCTCAGGAAACTATTACGGGTGGT
TCGACCGT

SEQ ID NO: 12 is the light chain amino acid sequence of K9-6N6.2.

EIVLTQSPATLSLSPGERATLSCRASQAVSSYLAWYQQKPGQAPRLLIYD
ASNRATGIPARFSGSGSGTDFTLTISSLEPEDFAVYYCQQRSNWPPAFGQ
GTKVEIKRNDAQPAVYLFQPSPDQLHTGSASVVCLLNSFYPKDINVKWKV
DGVIQDTGIQESVTEQDKDSTYSLSSTLTMSSTEYLSHELYSCEITHKSL
PSTLIKSFQRSECQRVD

SEQ ID NO: 13 is the nucleotide sequence encoding the light chain of K9-6N6.2.

AAGCTTGCCGCCACCATGGGTTGGTCCTGCATCATTCTGTTCCTGGTGGC
CACCGCTACAGGCGTGCACAGCGAAATCGTCCTGACCCAGTCTCCCGCCA
CACTGAGTCTGTCACCTGGCGAGAGAGCCACCCTGTCTTGTCGCGCTTCC
CAGGCCGTGTCCAGCTACCTGGCATGGTATCAGCAGAAGCCTGGACAGGC
CCCAAGACTGCTGATCTACGACGCTTCCAACCGAGCAACAGGGATTCCAG
CTCGTTTCTCTGGCAGTGGATCAGGGACTGACTTTACTCTGACCATCTCT
AGTCTGGAGCCCGAAGATTTCGCCGTGTACTATTGCCAGCAGCGGAGCAA
CTGGCCCCCTGCATTTGGTCAGGGCACCAAGGTGGAAATTAAACGCAATG
ACGCACAGCCTGCCGTCTACCTGTTCCAGCCAAGTCCCGATCAGCTGCAT
ACAGGCTCCGCCAGCGTGGTCTGTCTGCTGAACAGCTTTTATCCAAAGGA
CATCAATGTGAAGTGGAAAGTGGACGGAGTCATCCAGGATACTGGGATTC
AGGAGTCCGTCACCGAACAGGACAAAGATTCTACATATAGTCTGTCATCC
ACACTGACTATGAGCTCTACCGAGTACCTGAGTCACGAACTGTATTCATG
CGAGATCACTCATAAGTCACTGCCCTCCACCCTGATTAAGTCCTTCCAGA
GGTCTGAGTGTCAGCGGGTGGATTGAGAATTC

SEQ ID NO: 14 is the amino acid sequence of the light chain variable region of K9-6N6.2.

EIVLTQSPATLSLSPGERATLSCRASQAVSSYLAWYQQKPGQAPRLLIYD
ASNRATGIPARFSGSGSGTDFTLTISSLEPEDFAVYYCQQRSNWPPAFGQ
GTKVEIK

SEQ ID NO: 15 is the nucleotide sequence encoding the light chain variable region of K9-6N6.2.

GAAATCGTCCTGACCCAGTCTCCCGCCACACTGAGTCTGTCACCTGGCGA

GAGAGCCACCCTGTCTTGTCGCGCTTCCCAGGCCGTGTCCAGCTACCTGG

CATGGTATCAGCAGAAGCCTGGACAGGCCCCAAGACTGCTGATCTACGAC

GCTTCCAACCGAGCAACAGGGATTCCAGCTCGTTTCTCTGGCAGTGGATC

AGGGACTGACTTTACTCTGACCATCTCTAGTCTGGAGCCCGAAGATTTCG

CCGTGTACTATTGCCAGCAGCGGAGCAACTGGCCCCCTGCATTTGGTCAG

GGCACCAAGGTGGAAATTAAA

SEQ ID NO: 16 is the light chain CDR1 amino acid sequence of K9-6N6.2.

RASQAVSSYLA

SEQ ID NO: 17 is the nucleotide sequence encoding the light chain CDR1 amino acid sequence of K9-6N6.2.

CGCGCTTCCCAGGCCGTGTCCAGCTACCTGGCA

SEQ ID NO: 18 is the light chain CDR2 amino acid sequence of K9-6N6.2.

YDASNRAT

SEQ ID NO: 19 is the nucleotide sequence encoding the light chain CDR2 amino acid sequence of K9-6N6.2.

TACGACGCTTCCAACCGAGCAACA

SEQ ID NO: 20 is the light chain CDR3 amino acid sequence of K9-6N6.2.

QQRSNWPPA

SEQ ID NO: 21 is the nucleotide sequence encoding the light chain CDR3 amino acid sequence of K9-6N6.2.

CAGCAGCGGAGCAACTGGCCCCCTGCA

SEQ ID NO: 22 is the heavy chain amino acid sequence of K9-6N6.1.

QLQLQESGPGLVKPSETLSLTCTVSGGSINSSSYYWGWLRQSPGKGLEWI

GSFFYTGSTYYNPSLRSRLTISVDTSKNQFSLMLSSVTAADTAVYYCARQ

STYYYGSGNYYGWFDRWDQGTLVTVSSASTTAPSVFPLAPSCGSTSGSTV

ALACLVSGYFPEPVTVSWNSGSLTSGVHTFPSVLQSSGLYSLSSMVTVPS

SRWPSETFTCNVAHPASKTKVDKPVPKRENGRVPRPPDCPKCPAPEMLGG

PSVFIFPPKPKDTLLIARTPEVTCVVVDLDPEDPEVQISWFVDGKQMQTA

KTQPREEQFNGTYRVVSVLPIGHQDWLKGKQFTCKVNNKALPSPIERTIS

KARGQAHQPSVYVLPPSREELSKNTVSLTCLIKDFFPPDIDVEWQSNGQQ

EPESKYRTTPPQLDEDGSYFLYSKLSVDKSRWQRGDTFICAVMHEALHNH

YTQESLSHSPGK

SEQ ID NO: 23 is the nucleotide sequence encoding the heavy chain amino acid sequence of K9-6N6.1.

CAGCTGCAGCTGCAGGAGAGCGGACCTGGACTGGTCAAGCCATCTGAAAC

CCTGAGTCTGACCTGTACAGTGAGCGGCGGATCTATCAACTCCAGCTCTT

ACTATTGGGGCTGGCTGCGGCAGTCTCCAGGGAAAGGTCTGGAGTGGATT

GGGAGCTTCTTTTACACAGGTTCTACTTACTATAACCCCAGTCTGAGGTC

ACGGCTGACCATCTCAGTGGACACATCCAAGAATCAGTTTTCCCTGATGC

TGAGTTCAGTCACAGCCGCTGATACTGCCGTGTACTATTGCGCTCGACAG

AGTACCTACTATTACGGCTCAGGAAACTATTACGGGTGGTTCGACCGTTG

GGATCAGGGTACCCTGGTCACAGTGTCCAGCGCAAGCACCACAGCACCAT

CCGTGTTCCCCCTGGCCCCTAGCTGCGGGAGTACCTCAGGTTCCACAGTC

GCTCTGGCATGTCTGGTGAGTGGGTATTTCCCTGAGCCAGTCACCGTGTC

ATGGAATAGCGGCTCTCTGACTTCTGGAGTCCACACCTTTCCTAGTGTGC

TGCAGTCTAGTGGCCTGTACTCTCTGTCATCCATGGTCACTGTGCCCAGC

TCCAGGTGGCCTTCTGAAACTTTCACCTGCAACGTGGCCCATCCAGCTAG

TAAGACAAAAGTGGACAAGCCCGTGCCTAAACGCGAGAATGGAAGAGTGC

CACGCCCCCCTGATTGCCCCAAGTGTCCAGCTCCCGAAATGCTGGGGGGT

CCTTCCGTGTTCATCTTTCCACCCAAGCCAAAAGACACCCTGCTGATTGC

AAGAACTCCTGAGGTGACCTGCGTGGTCGTGGACCTGGACCCCGAGGACC

CCGAAGTCCAGATTTCCTGGTTCGTGGATGGGAAGCAGATGCAGACTGCC

AAAACCCAGCCCAGAGAGGAACAGTTTAACGGTACATATCGCGTCGTGAG

CGTGCTGCCTATCGGCCACCAGGACTGGCTGAAGGGAAAACAGTTTACAT

GCAAGGTGAACAATAAAGCTCTGCCTTCACCAATCGAGAGGACTATTTCC

AAGGCTCGGGGACAGGCACATCAGCCCAGCGTCTATGTGCTGCCTCCAAG

TCGAGAGGAACTGTCAAAGAACACAGTGTCCCTGACTTGTCTGATCAAAG

ATTTCTTTCCCCCTGACATTGATGTGGAGTGGCAGAGCAATGGCCAGCAG

GAGCCTGAATCTAAGTACCGCACTACCCCACCCCAGCTGGACGAAGATGG

CAGCTATTTCCTGTACTCCAAGCTGAGCGTGGACAAATCTCGATGGCAGC

GTGGAGATACCTTTATCTGTGCAGTGATGCACGAGGCCCTGCACAATCAT

TACACACAAGAAAGTCTGTCACATTCCCCCGGCAAG

SEQ ID NO: 24 is the light chain amino acid sequence of K9-6N6.1.

EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPAFGQ

GTKVEIKRNDAQPAVYLFQPSPDQLHTGSASVVCLLNSFYPKDINVKWKV

DGVIQDTGIQESVTEQDKDSTYSLSSTLTMSSTEYLSHELYSCEITHKSL

PSTLIKSFQRSECQRVD

SEQ ID NO: 25 is the nucleotide sequence encoding the light chain amino acid sequence of K9-6N6.1.

GAAATCGTCCTGACCCAGTCTCCCGCCACACTGAGTCTGTCACCTGGCGA

GAGAGCCACCCTGTCTTGTCGCGCTTCCCAGAGCGTGTCCAGCTACCTGG

CATGGTATCAGCAGAAGCCTGGACAGGCCCCAAGACTGCTGATCTACGAC

GCTTCCAACCGAGCAACAGGGATTCCAGCTCGTTTCTCTGGCAGTGGATC

AGGGACTGACTTTACTCTGACCATCTCTAGTCTGGAGCCCGAAGATTTCG

CCGTGTACTATTGCCAGCAGCGGAGCAACTGGCCCCCTGCATTTGGTCAG

GGCACCAAGGTGGAAATTAAACGCAATGACGCACAGCCTGCCGTCTACCT

GTTCCAGCCAAGTCCCGATCAGCTGCATACAGGCTCCGCCAGCGTGGTCT

GTCTGCTGAACAGCTTTTATCCAAAGGACATCAATGTGAAGTGGAAAGTG

GACGGAGTCATCCAGGATACTGGGATTCAGGAGTCCGTCACCGAACAGGA

CAAAGATTCTACATATAGTCTGTCATCCACACTGACTATGAGCTCTACCG

AGTACCTGAGTCACGAACTGTATTCATGCGAGATCACTCATAAGTCACTG

CCCTCCACCCTGATTAAGTCCTTCCAGAGGTCTGAGTGTCAGCGGGTGGA

T

SEQ ID NO: 26 is the heavy chain amino acid sequence of Olaratumab.

QLQLQESGPGLVKPSETLSLTCTVSGGSINSSSYYWGWLRQSPGKGLEWI

GSFFYTGSTYYNPSLRSRLTISVDTSKNQFSLMLSSVTAADTAVYYCARQ

STYYYGSGNYYGWFDRWDQGTLVTVSSASTKGPSVFPLAPSSKSTSGGTA

ALGCLVKDYFPEPVTVSWNSGALTSGVHTFPAVLQSSGLYSLSSVVTVPS

SSLGTQTYICNVNHKPSNTKVDKRVEPKSCDKTHTCPPCPAPELLGGPSV

FLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAK

GQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKS

LSLSPGK

SEQ ID NO: 27 is the nucleotide sequence encoding the heavy chain amino acid sequence of Olaratumab.

CAGCTGCAGCTGCAGGAGTCGGGCCCAGGACTGGTGAAGCCTTCGGAGAC

CCTGTCCCTCACCTGCACTGTCTCTGGTGGCTCCATCAACAGTAGTAGTT

ACTACTGGGGCTGGCTCCGCCAGTCCCCAGGGAAGGGGCTGGAGTGGATT

GGGAGTTTCTTTTATACTGGGAGCACCTACTACAACCCGTCCCTCAGGAG

TCGACTCACCATATCCGTAGACACGTCCAAGAACCAGTTCTCCCTGATGC

TGAGTTCTGTGACCGCCGCAGACACGGCTGTATATTACTGTGCGAGACAG

TCCACGTATTACTATGGTTCGGGGAATTATTATGGCTGGTTCGACCGCTG

GGACCAGGGAACCCTGGTCACCGTCTCCTCAGCTAGCACCAAGGGCCCAT

CGGTCTTCCCCCTGGCACCCTCCTCCAAGAGCACCTCTGGGGGCACAGCG

GCCCTGGGCTGCCTGGTCAAGGACTACTTCCCCGAACCGGTGACGGTGTC

GTGGAACTCAGGCGCCCTGACCAGCGGCGTGCACACCTTCCCGGCTGTCC

TACAGTCCTCAGGACTCTACTCCCTCAGCAGCGTGGTGACCGTGCCCTCC

AGCAGCTTGGGCACCCAGACCTACATCTGCAACGTGAATCACAAGCCCAG

CAACACCAAGGTGGACAAGAGAGTTGAGCCCAAATCTTGTGACAAAACTC

ACACATGCCCACCGTGCCCAGCACCTGAACTCCTGGGGGGACCGTCAGTC

TTCCTCTTCCCCCCAAAACCCAAGGACACCCTCATGATCTCCCGGACCCC

TGAGGTCACATGCGTGGTGGTGGACGTGAGCCACGAAGACCCTGAGGTCA

AGTTCAACTGGTACGTGGACGGCGTGGAGGTGCATAATGCCAAGACAAAG

CCGCGGGAGGAGCAGTACAACAGCACGTACCGTGTGGTCAGCGTCCTCAC

CGTCCTGCACCAGGACTGGCTGAATGGCAAGGAGTACAAGTGCAAGGTCT

CCAACAAAGCCCTCCCAGCCCCCATCGAGAAAACCATCTCCAAAGCCAAA

GGGCAGCCCCGAGAACCACAGGTGTACACCCTGCCCCCATCCCGGGAGGA

GATGACCAAGAACCAGGTCAGCCTGACCTGCCTGGTCAAAGGCTTCTATC

CCAGCGACATCGCCGTGGAGTGGGAGAGCAATGGGCAGCCGGAGAACAAC

TACAAGACCACGCCTCCCGTGCTGGACTCCGACGGCTCCTTCTTCCTCTA

TAGCAAGCTCACCGTGGACAAGAGCAGGTGGCAGCAGGGGAACGTCTTCT

CATGCTCCGTGATGCATGAGGCTCTGCACAACCACTACACGCAGAAGAGC

CTCTCCCTGTCCCCGGGTAAA

SEQ ID NO: 28 is the light chain amino acid sequence of Olaratumab.

EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPAFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

SEQ ID NO: 29 is the nucleotide sequence encoding the light chain amino acid sequence of Olaratumab.

GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGCGTAGCAACTGGCCTCCGGCGTTCGGCCAA

GGGACCAAGGTGGAAATCAAACGTACGGTGGCTGCACCATCTGTCTTCAT

CTTCCCGCCATCTGATGAGCAGTTGAAATCTGGAACTGCCTCTGTTGTGT

GCCTGCTGAATAACTTCTATCCCAGAGAGGCCAAAGTACAGTGGAAGGTG

GATAACGCCCTCCAATCGGGTAACTCCCAGGAGAGTGTCACAGAGCAGGA

-continued

CAGCAAGGACAGCACCTACAGCCTCAGCAGCACCCTGACGCTGAGCAAAG

CAGACTACGAGAAACACAAAGTCTACGCCTGCGAAGTCACCCATCAGGGC

CTGAGCTCGCCCGTCACAAAGAGCTTCAACAGGGGAGAGTGT

SEQ ID NO: 30 is the heavy chain variable region amino acid sequence of Olaratumab.

QLQLQESGPGLVKPSETLSLTCTVSGGSINSSSYYWGWLRQSPGKGLEWI

GSFFYTGSTYYNPSLRSRLTISVDTSKNQFSLMLSSVTAADTAVYYCARQ

STYYYGSGNYYGWFDRWDQGTLVTVSS

SEQ ID NO: 31 is the nucleotide sequence encoding the heavy chain variable region amino acid sequence of Olaratumab.

CAGCTGCAGCTGCAGGAGTCGGGCCCAGGACTGGTGAAGCCTTCGGAGAC

CCTGTCCCTCACCTGCACTGTCTCTGGTGGCTCCATCAACAGTAGTAGTT

ACTACTGGGGCTGGCTCCGCCAGTCCCCAGGGAAGGGGCTGGAGTGGATT

GGGAGTTTCTTTTATACTGGGAGCACCTACTACAACCCGTCCCTCAGGAG

TCGACTCACCATATCCGTAGACACGTCCAAGAACCAGTTCTCCCTGATGC

TGAGTTCTGTGACCGCCGCAGACACGGCTGTATATTACTGTGCGAGACAG

TCCACGTATTACTATGGTTCGGGGAATTATTATGGCTGGTTCGACCGCTG

GGACCAGGGAACCCTGGTCACCGTCTCCTCA

SEQ ID NO: 32 is the light chain variable region amino acid sequence of Olaratumab.

EIVLTQSPATLSLSPGERATLSCRASQSVSSYLAWYQQKPGQAPRLLIYD

ASNRATGIPARFSGSGSGTDFTLTISSLEPEDFAVYYCQQRSNWPPAFGQ

GTKVEIK

SEQ ID NO: 33 is the nucleotide sequence encoding the light chain variable region amino acid sequence of Olaratumab.

GAAATTGTGTTGACACAGTCTCCAGCCACCCTGTCTTTGTCTCCAGGGGA

AAGAGCCACCCTCTCCTGCAGGGCCAGTCAGAGTGTTAGCAGCTACTTAG

CCTGGTACCAACAGAAACCTGGCCAGGCTCCCAGGCTCCTCATCTATGAT

GCATCCAACAGGGCCACTGGCATCCCAGCCAGGTTCAGTGGCAGTGGGTC

TGGGACAGACTTCACTCTCACCATCAGCAGCCTAGAGCCTGAAGATTTTG

CAGTTTATTACTGTCAGCAGCGTAGCAACTGGCCTCCGGCGTTCGGCCAA

GGGACCAAGGTGGAAATCAAA

SEQ ID NO: 34 is the heavy chain CDR1 amino acid sequence of Olaratumab.

TVSGGSINSSSYYWG

SEQ ID NO: 35 is the heavy chain CDR2 amino acid sequence of Olaratumab.

SFFYTGSTYYNPSLRS

SEQ ID NO: 36 is the heavy chain CDR3 amino acid sequence of Olaratumab.

ARQSTYYYGSGNYYGWFDR

SEQ ID NO: 37 is the light chain CDR1 amino acid sequence of Olaratumab.

RASQSVSSYLA

SEQ ID NO: 38 is the light chain CDR2 amino acid sequence of Olaratumab.

YDASNRAT

SEQ ID NO: 39 is the light chain CDR3 amino acid sequence of Olaratumab.

QQRSNWPPA

What is claimed is:

1. A monoclonal antibody comprising a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, wherein the amino acid sequence of LCDR1 is given by SEQ ID NO:16, the amino acid sequence of LCDR2 is given by SEQ ID NO: 18, the amino acid sequence of LCDR3 is given by SEQ ID NO: 20, the amino acid sequence of HCDR1 is given by SEQ ID NO: 6, the amino acid sequence of HCDR2 is given by SEQ ID NO: 8, and the amino acid sequence of HCDR3 is given by SEQ ID NO: 10; and wherein the monoclonal antibody binds canine platelet derived growth factor receptor alpha (cPDGFRA).

2. The monoclonal antibody of claim 1, comprising a light chain variable region (LCVR) and a heavy chain variable region (HCVR), wherein the amino acid sequence of the LCVR is given by SEQ ID NO: 14 and the amino acid sequence of the HCVR is given by SEQ ID NO: 4.

3. The monoclonal antibody of claim 1, comprising a light chain (LC) and a heavy chain (HC), wherein the amino acid sequence of the LC is given by SEQ ID NO: 12 and the amino acid sequence of the HC is given by SEQ ID NO: 1.

4. A method of treating osteosarcoma in a canine, comprising administration of the monoclonal antibody of claim 1 to a canine in need thereof.

5. A method of treating osteosarcoma in a canine, comprising administration of the monoclonal antibody of claim 2 to a canine in need thereof.

6. A method of treating osteosarcoma in a canine, comprising administration of the monoclonal antibody of claim 3 to a canine in need thereof.

* * * * *